United States Patent [19]

Emerson, Jr. et al.

[11] Patent Number: 4,829,054
[45] Date of Patent: May 9, 1989

[54] METHOD OF DECREASING LUNG DAMAGE IN A HOST FOLLOWING THE ONSET OF GRAM NEGATIVE SEPTICEMIA/ENDOTOXEMIA

[75] Inventors: Thomas E. Emerson, Jr., Berkeley; Thomas B. Redens, Oakland, both of Calif.

[73] Assignee: Miles Laboratories, Inc., Elkhart, Ind.

[21] Appl. No.: 37,675

[22] Filed: Apr. 13, 1987

[51] Int. Cl.$^4$ .............................................. A61K 37/64
[52] U.S. Cl. ...................................... 514/21; 514/886; 514/921; 514/2; 424/94.2; 424/94.64
[58] Field of Search ......................... 514/21, 886, 921; 424/94.2, 94.64

[56] References Cited

PUBLICATIONS

Fritz et al CA 94, 1981, #17257w.
Jachum et al, CA 100, 1984, #136794c.
Okamoto et al, CA 103, 1985, #153649p.
Fuchs et al CA 102, 1985, #3692m.
Koide et al CA 93, 1980 #3030r.
Gitel et al CA 101, 1984, #36651p.
El et al CA 105, 1986, #205150g.
Stockley et al CA 101, 1984, #2741v.

*Primary Examiner*—Margaret Moskowitz
*Assistant Examiner*—Garnette D. Draper
*Attorney, Agent, or Firm*—James A. Giblin; Pamela A. Simonton

[57] ABSTRACT

There is disclosed a process for treating gram negative septicemia/endotoxemia to decrease lung damage in a host by parenterally administering a therapeutically effective amount of antithrombin III and alpha-1-proteinase inhibitor.

9 Claims, 4 Drawing Sheets

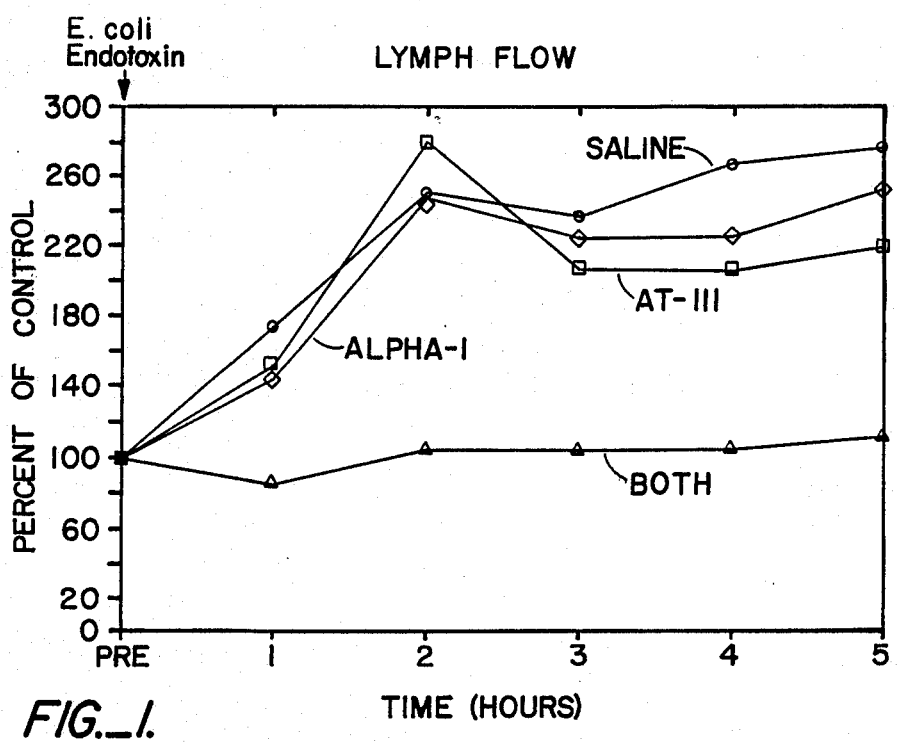
FIG._1.
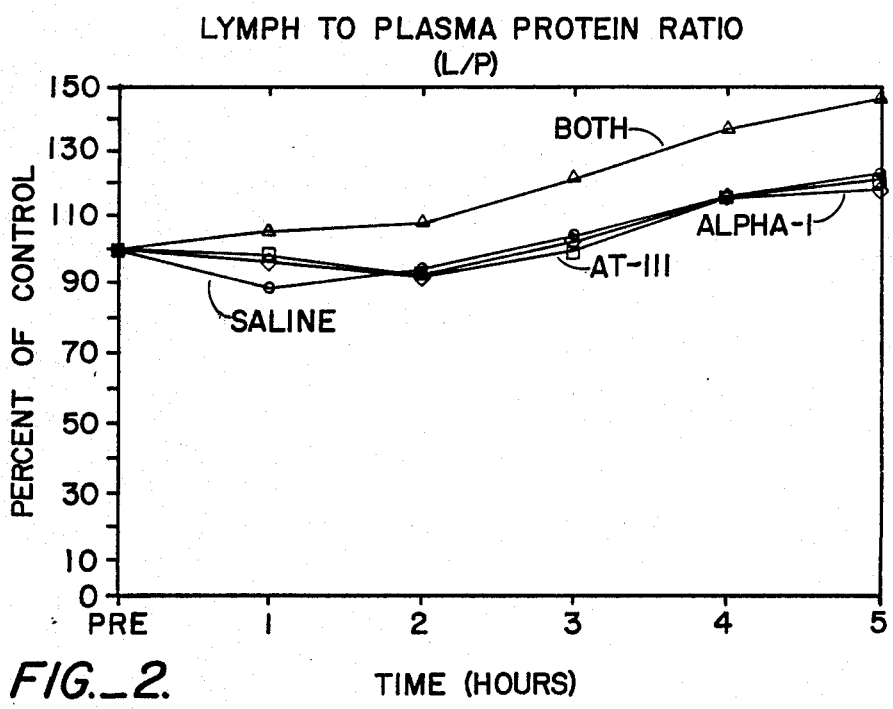
FIG._2.

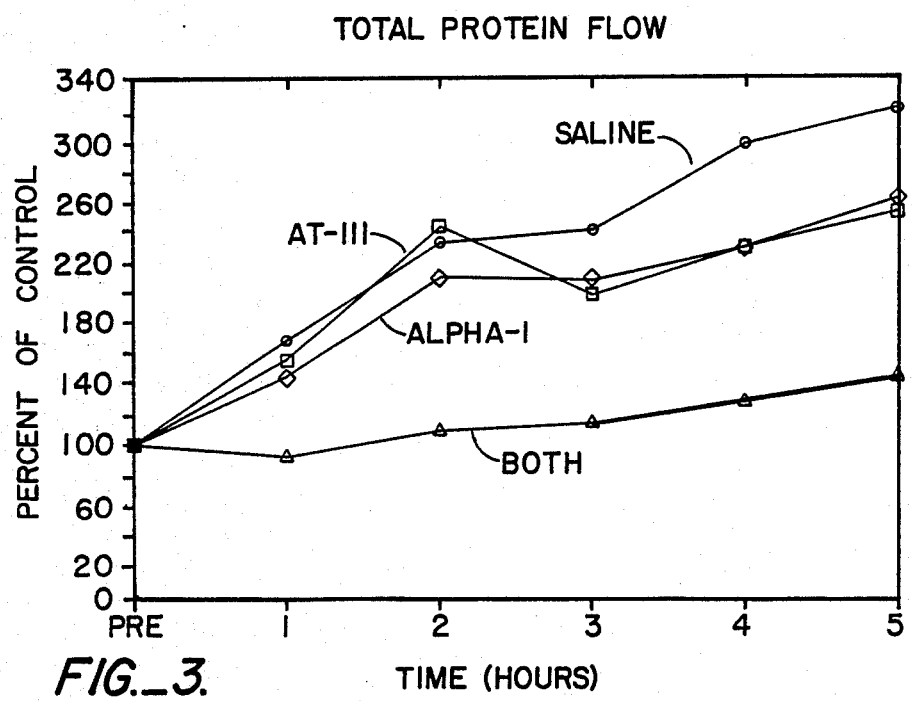
FIG._3.
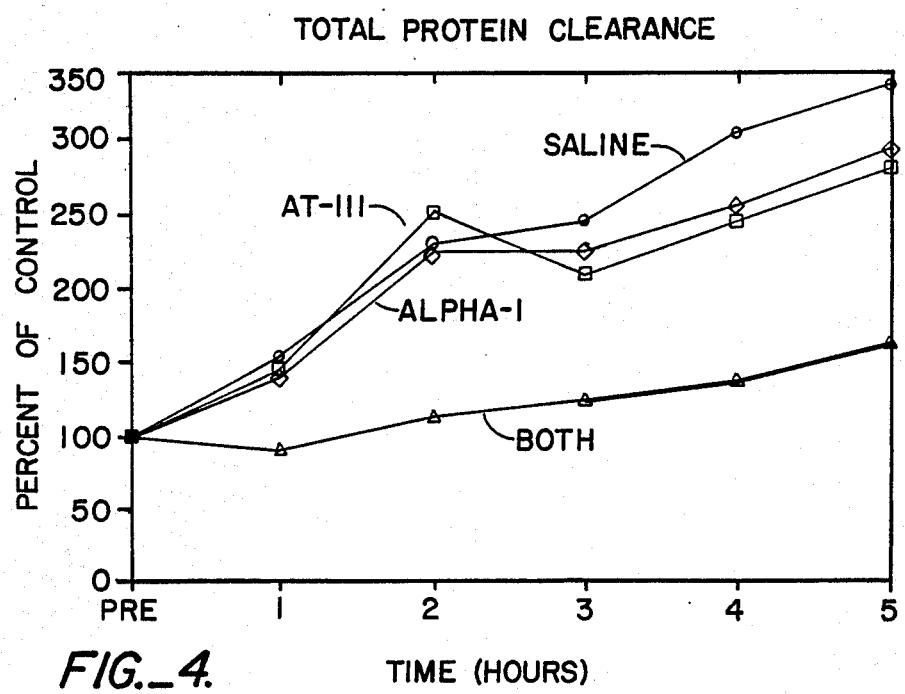
FIG._4.

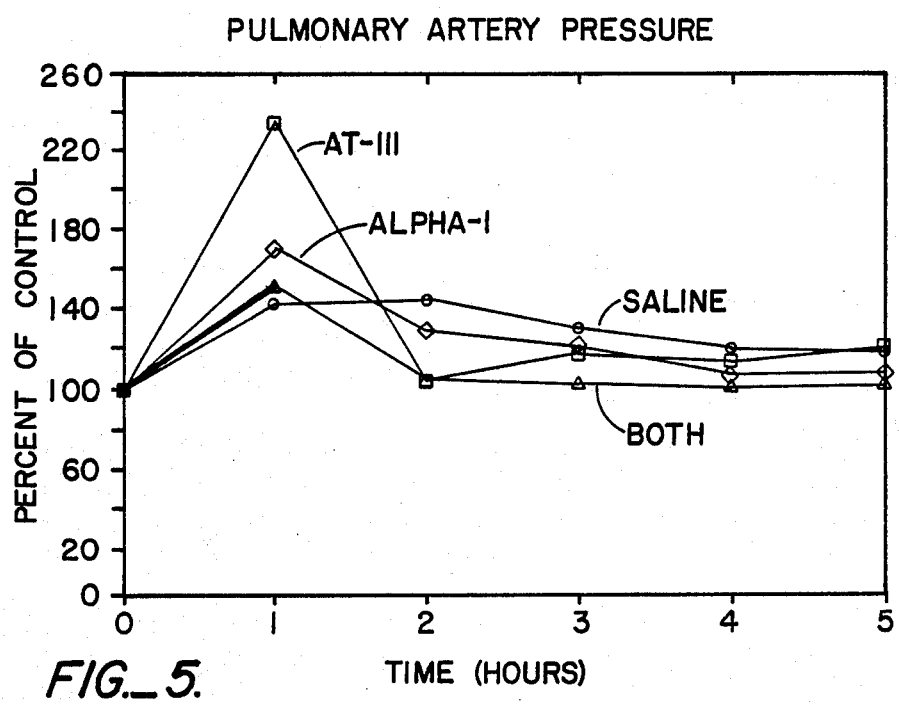
FIG._5.
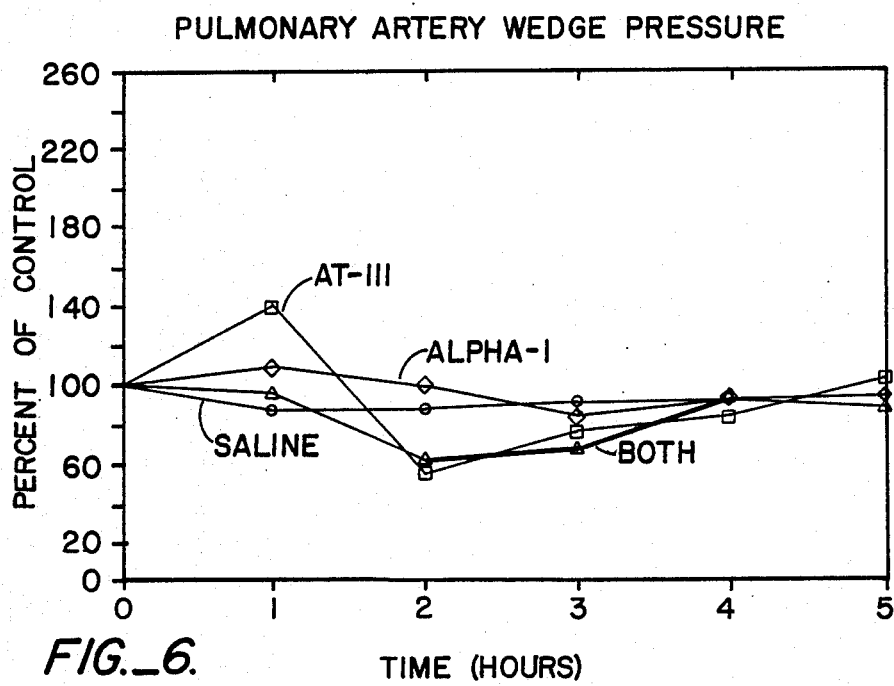
FIG._6.

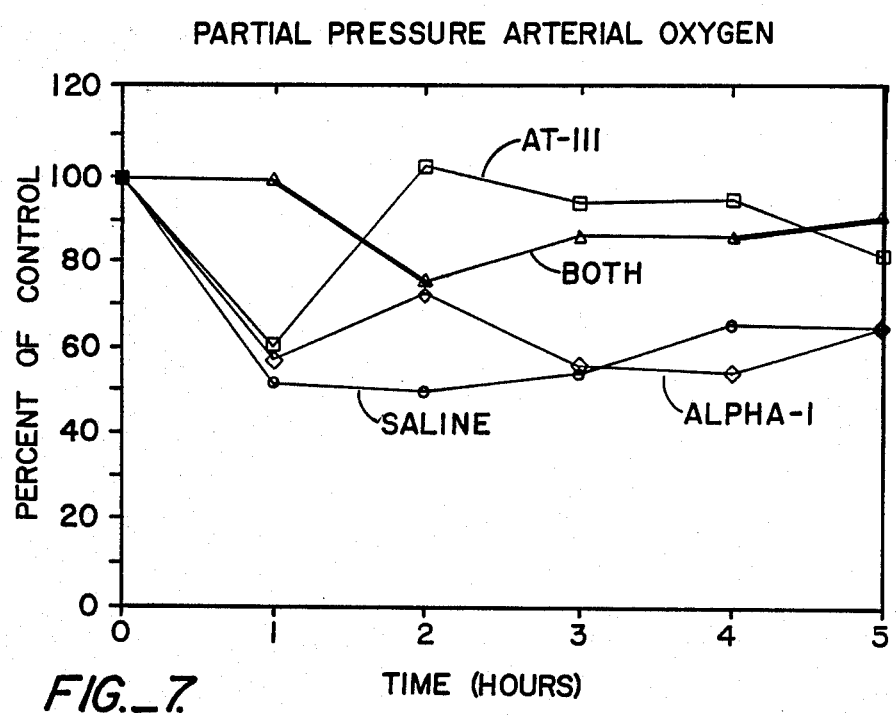
FIG._7

METHOD OF DECREASING LUNG DAMAGE IN A HOST FOLLOWING THE ONSET OF GRAM NEGATIVE SEPTICEMIA/ENDOTOXEMIA

BACKGROUND OF THE INVENTION

1. Field of the Invention

This invention relates to a method for decreasing lung damage in a host following the onset of gram negative septicemia/endotoxemia. The method of treatment comprises parenterally administering therapeutically effective amounts of antithrombin III and alpha-1-proteinase inhibitor.

The publications and other materials used to illuminate the background of the invention, and in particular cases, to provide additional details concerning its practice are incorporated herein by reference and listed at the end of the Specification in the form of a bibliography.

The adult respiratory distress syndrome (ARDS) is often associated with septicemia/endotoxemia, peritonitis, acute pancreatitis, fat emboli, aspiration pneumonitis, atelectasis, pulmonary emboli, pneumonia and other illnesses (1). Although an accurate accounting of the incidence of ARDS is unavailable, a government task force arrived at a conservative figure of at least 150,000 cases per year (2). At the present time, an effective treatment for ARDS associated with gram-negative sepsis still eludes the clinician. The serious impact of this on patient mortality is further emphasized by the observation that approximately two-thirds of patients dying in shock following resuscitation, or dying post-operatively die with ARDS (1).

Disseminated Intravascular Coagulation (DIC) is an early precursor associated with sepsis and shock leading to ARDS (3). It has been shown that DIC occurs quite early in sepsis, and that in fact it precedes the many other perturbations seen in the cardiovascular, metabolic, endocrine, and immunological systems (3). DIC is directly associated with a rapid consumption of clotting factors, as well as antithrombin-III (AT-III), a major inhibitor of the clotting system (4-9). Other studies have shown that when levels of AT-III decrease to below 70% of normal, the prognosis is grim (10). However, prophylaxis or pretreatment with high doses of AT-III (250 $\mu$/kg) has been shown to markedly increase survival in severely *E. coli* endotoxemic rats (3) and in fact to ameliorate indices of DIC in these endotoxemic rats and in the *Klebsiella peritonitis* rat model (11).

Margination and adhesion of polymorphonuclear leukocytes (PMN) to lung vessel endothelial cells, infiltration of PMN's into the lung extravascular space, and their subsequent release of elastase, oxygen free radicals, and other harmful substances also occurs early during the course of sepsis (13-17). Bronchoalveolar lavage (BAL) fluid from ARDS patients has been shown to contain PMN elastase (18), inactivated alpha-1-proteinase inhibitor (alpha-1-PI), and elastase-alpha-1-PI complexes (19).

In cases of impending sepsis and shock, prophylactic administration of AT-III and alpha-1-PI should be beneficial in preventing or at least attenuating the pulmonary damage associated with ARDS.

AT-III and alpha-1-PI should each provide protection within their respective range of function, and combining them results in an additive or synergistic benefit by: (1) inhibiting DIC and thus preventing reticuloendothelial system (RES) depression and allowing effective bacterial and/or microaggregate clearance; (2) inhibiting DIC and the subsequent plugging of lung microvessels by fibrin microaggregates; (3) inactivating neutrophil elastase and thus preventing lung vascular endothelial and alveolar tissue damage; and (4) protecting AT-III (20, 21) from inactivation by PMN elastase. The use of AT-III and alpha-1-PI combined for treatment of pulmonary dysfunction during inflammatory conditions such as gram-negative endotoxemia or septicemia has not been previously reported by others.

The present study was therefore completed to test the following hypotheses in the gram-negative endotoxemic sheep pulmonary dysfunction model: (1) alpha-1-PI supplementation alone limits the pulmonary damage; (2) AT-III supplementation alone limits the pulmonary damage; (3) the combination of AT-III and alpha-1-PI supplementation prevents or limits the pulmonary damage, and this efficacy is either additive or synergistic.

Results of the present study do not support our first hypothesis, weakly support our second hypothesis and strongly support our third.

SUMMARY OF THE INVENTION

The invention described therein is a method for treating a host following the onset of gram negative septicemia/endotoximia. In the present method, the combined therapy of therapeutically effective amounts of antithrombin III and alpha-1-proteinase inhibitor have prevented lung damage in a host. Prophylactic administration of the combined therapy ameliorates pulmonary dysfunction, avoiding the severe pulmonary complications which often arise following the onset of septicemia/endotoxemia.

BRIEF DESCRIPTION OF THE DRAWING

FIG. 1 is a graph showing a comparison of average lymph flow.

FIG. 2 is a graph showing a comparison of lymph/plasma protein concentration ratio (L/P).

FIG. 3 is a graph showing a comparison of average pulmonary artery pressures.

FIG. 4 is a graph showing a comparison of average pulmonary artery wedge pressures.

FIG. 5 is a graph showing a comparison of average transvascular protein flow.

FIG. 6 is a graph showing a comparison of average transvascular protein clearance.

FIG. 7 is a graph showing a comparison of average arterial oxygen tensions.

DETAILED DESCRIPTION OF THE INVENTION

The method of the present invention is a treatment for decreasing lung damage in a mammal following the onset of gram negative septicemia/endotoxemia from such gram negative bacteria for example, *Escherichia coli*, *Klebsiella pneumoniae*, and *Pseudomonas aeruginosa*. The treatment involves a combined therapy of parenterally administering therapeutically effective amounts of antithrombin III and alpha-1-proteinase inhibitor. The combined therapy increases the plasma functional activity level of antithrombin III to above 100% of normal and the level of alpha-1-proteinase inhibitor to above 100% of normal. A plurality of treatment doses may be necessary to maintain the antithrombin III and alpha-1-proteinase inhibitor at therapeutically effective levels.

Materials and Methods

The AT-III and alpha-1-PI used in this study were prepared at Cutter Laboratories (Berkeley, CA). The AT-III was purified from pooled human plasma by adsorption on fixed heparin by a modification of the technique of Miller-Andersson et al. (23). Final characterization of the AT-III demonstrated that it contained less than 0.01 μ/ml heparin, was sterile, pyrogen free, and fully active by a number of functional tests (unpublished observations, Dr. Robert Jordan, Biochemistry Research, Cutter Laboratories). The alpha-1-PI was purified from pooled human plasma using the Cohn fraction IV-1 paste by polyethylene glycol precipitation and DEAE-Sepharose chromatography (24). The final characterization of the alpha-1-PI product showed it to be sterile, nonpyrogenic, and behave almost identically to alpha-1-PI in plasma.

Animals

Twenty four male or wether range sheep weighing 25–35 kg were used in this study. The sheep were carefully examined prior to use for signs of illness and/or injury.

Surgical Protocol

The animals were prepared for collecting lymph from the efferent duct of the mediastinal lymph node by the method of Staub's group (25, 26). The sheep were fasted for two days, and water was withheld for one day prior to surgery. The animals were given atropine sulfate (1.08 mg/kg, iv) immediately prior to being obtunded with thiamylal sodium (15 mg/kg, iv), intubated, placed in a right lateral recumbency, and maintained on 1–2% halothane in 40% oxygen, 60% nitrogen. The anesthesia was delivered via an anesthetic ventilator (Ohio Medical Products, Madison, Wisconsin) set at an end inspiratory pressure of 30 cm water. If the sheep began showing signs of respiratory distress, as manifested by a reduced tidal volume, the end expiratory pressure was increased to as high as 40 cm water. The sheep were then given 500 ml of 5% dextrose iv. The efferent duct of the caudal mediastinal lymph node was catheterized for pulmonary lymph collection using the technique described by Staub et al (25, 26). Upon pneumothorax, the sheep was placed on positive end expiratory pressure of 4 cm water.

The surgical procedure consisted of 2 thoracotomies, the first in the ninth interspace. The mediastinal lymph node was tied and then resected caudally to the pulmonary ligament, and any afferent diaphragmatic or chest wall lympatics feeding into the node were cauterized. The second thoracotomy consisted of an incision in the fourth or fifth interspace. The efferent duct of the caudal mediastinal lymph node was identified via injection of 0.2 ml of 1% Evans blue dye directly into the mediastinal lymph node with a 30 gauge needle. The efferent duct was then tied cranial to the point of catheterization. A heparin coated silastic tubing catheter was inserted into the duct and tied in place (catheter tubing heparinized with TDMAC 2% heparin complex, Polysciences, Inc., Warrington, PA) and the free end was exteriorized for lymph collection. A chest tube was inserted prior to incision closure for removal of air. Incision sites were closed in three layers to prevent pneumothorax.

A polyethylene catheter was inserted into the right carotid artery to the level of the ascending aorta for measurement of arterial blood pressure (ABP) and heart rate (HR) and for anaerobic removal of arterial blood. A Swan-Ganz 7-F thermodilution catheter was inserted into the right jugular vein and advanced into a pulmonary artery branch for measurement of central venous, pulmonary artery and pulmonary artery wedge pressures (CV, PAP, PAWP, respectively).

Experimental Protocol

The sheep were randomized into four groups. Group 1 received AT-III (250 u/kg, Cutter Laboratories, Lots PR2966 and PR03B007) and alpha-1-PI (100 mg/kg, Cutter Laboratories, Lot PR3008). Group 2 received AT-III only (same dosage and lot number as above) and saline (to qs volume to that of AT-III and alpha-1-PI). Group 3 received alpha-1-PI only (same dosage and lot number as group 1) and saline (to qs volume to that of AT-III and alpha-1-PI). Group 4 received only saline in volume equivalent to that of AT-III and alpha-1-PI.

Pretreatments were delivered intravenously over a 1 hour period prior to surgery. Post-treatment measurements were taken after a 2 hour lymph-flow stabilization period. The physiological parameters ABP, HR, CBP, PAP, PAWP, cardiac output (CO), and lymph flow (Ql) were measured. Cardiac output was measured with an American Edwards model 9520A thermodilution cardiac output computer using iced saline as the injectate. Lymph flow was measured directly by 1 hour collections in preweighed tubes. Blood and lymph analysis consisted of the following: Arterial blood pH, pO2, pCO2, and hemoglobin concentration (Hb) were measured, and HC03, base excess (BE), and oxygen content ($O_2Ct$) were calculated via a Radiometer ABL3 blood gas analyzer. Arterial blood glucose and lactate were measured with Yellow Springs glucose and lactate analyzers (models 23A and 23L, respectively). Lymph and plasma protein concentrations (Lpro and Ppro, respectively) were measured with an American Opticals refractometer, model 10400A. The following parameters were calculated: stroke volume (SV)=CO/HR, total peripheral resistance (TPR)=ABP/CO, lymph/plasma protein concentration ratio (L/P)=Lpro/Ppro, pulmonary vascular resistance (PVR)=PAP-PAWP/CO, transvascular protein clearance (TPC)=Q1×Lpro/Ppro, and transvascular protein flow (TPF) =(Lpro×Q1)/100. Following these measurements, an E. coli endotoxin (Lipopolysaccharide B, Difco Lot 728547) challenge of 2 μg/kg was administered over a 45 minute period. Post challenge measurements were taken at 1, 2, 3, 4 and 5 hours. Following the five hour measurements, the sheep was euthanized by barbituate overdose.

Between group comparisons were calculated using an analysis of variance (ANOVA) test at each time point with the baseline values subtracted out, and within group comparisons were calculated using a paired Student's T-Test. P values of 0.05 or less were considered statistically significant.

Infusion of 2 μg/kg E. Coli endotoxin in each group resulted in the typical bi-phasic pulmonary artery pressure response early hypertension followed by a return towards normotension by the second hour. The early hypertensive stage is well characterized as a prostaglandin mediated response, as demonstrated by others (15, 16, 27–29). The well characterized lymph flow phenomenon also occured; a rapid increase in flow of dilute lymph, a result of the pulmonary hypertension, and the subsequent continued increase in flow with increasing lymph protein concentration. The secondary lymph response, increasing flow and protein concentration, appears to involve PMN leukocytes, as others have blocked the increase in protein-rich pulmonary lymph by inducing granulocytopenia prior to experimentation (17, 30, 31). This response did not occur with the AT-III/alpha-1-PI group.

Aside from the quantitative measurements taken, we noted qualitatively that, on the average, the AT-III/alpha-1-PI treatment animals exhibited less respiratory distress than animals in the other 3 treatment groups. This was manifested by their maintenance of normal pulmonary compliance (as measured by less inspiratory pressure required to reach a satisfactory tidal volume), and prevention of a decrease in arterial P02. Also, arterial P02 was maintained by increasing the inspiratory pressure in the AT-III alone group, but not in the alpha-1-PI alone or saline groups. FIG. 1 is a graph showing average lymph flows at each hour for each of the four groups. The AT-III/alpha-1-PI is significantly lower than AT-III alone, alpha-1-PI alone, or saline alone through 4 hours. At hour 5, AT-III/alpha-1-PI is significantly lower than alpha-1-PI alone and saline alone. Within group comparison shows that lymph flow in the AT-III/alpha-1-PI group did not increase significantly from 0–5 hours of endotoemia ($P<0.05$), whereas it increased significantly in the other three groups ($P<0.05$).

FIG. 2 is a graph depicting average L/P ratios at each hour for each of the four groups. At hours 1 and 2, the L/P ratio in the AT-III/alpha-1-PI group is significantly greater than the saline group ($P<0.05$). At hour 3, the L/P ratio in the AT-III/alpha-1-PI is significantly greater that the 3 other groups ($P<0.05$), and at hour 5, the L/P ratio in the AT-III/alpha-1-PI is significantly higher than the alpha-1-PI and saline groups ($P<0.05$). Within group comparison shows that all four groups increased significantly from 0 hours to 5 hours post endotoxin ($P<0.05$).

FIGS. 3 and 4 are graphs showing average transvascular protein flow and transvascular protein clearance for all groups during 5 hours of endotoxemia. At hours 1 and 2 (for both figures), the TVPF and TVPC in the AT-III/alpha-1-PI group was significantly lower than all other groups ($P<0.05$). At hour 3 (for both figures), the TVPF and TVPC in the AT-III/alpha-1-PI group was significantly lower than the alpha-1-PI and saline groups ($P<0.05$). At hour 4 (for both figures), the TVPF and TVPC in the AT-III/alpha-1-PI was significantly lower than the saline treatment group ($P<0.05$). Within group comparison (for both figures) shows that all four groups increased significantly from 0 hours to 5 hours post-endotoxin ($P<0.05$).

FIG. 5 is a graph showing average pulmonary artery pressures for all groups during 5 hours of endotoxemia. PAP was increased in all groups at hour 1, the increase being highest in the AT-III alone group ($P<0.05$). The elevated PAP waned in each group from 2–5 hours of endotoxemia: individually, PAP was not different from control, pre-endotoxin level in the AT-III/alpha-1-PI group ($P<0.05$), and was modestly above pre-endotoxin level in the other groups. This modest elevation was significant only in the AT-III alone and saline groups ($P<0.05$).

FIG. 6 is a graph showing average pulmonary artery wedge pressures for all groups during 5 hours of endotoxemia. No statistically significant differences exist between any groups at any given time point ($P<0.05$). Within group comparison showed that none of the four groups changed significantly from 0 hours to 5 hours post-endotoxin ($P>0.05$).

FIG. 7 shows average values for systemic arterial P02 during 5 hours of endotoxemia. Arterial P02 was not significantly different from the pre-endotoxin level in the AT-III/alpha-1-PI group at 1 or 3–5 hours of endotoxemia ($P>0.05$); there was no decrease in apparent lung compliance. In the AT-III alone group, P02 decreased markedly at 1 hour ($P>0.05$) but was increased to a level not different from pre-endotoxin level ($P>0.05$) from hours 2–4 by increasing the inspiratory gas pressure by 10 cm water. In the alpha-1-PI alone and saline groups, P02 decreased significantly by one hour of endotoxemia and remained depressed for the 5 hour protocol ($P>0.05$) despite increasing the inspiratory gas pressure to 40 cm water. Given the above disclosures, it is thought variations will occur to those skilled in the art. Accordingly, it is intended that the above examples should be construed as illustrative only and that the scope of the inventions disclosed should be limited only by the following claims.

REFERENCES

1. Shoemaker W. C.: Controversies in the pathophysiology and fluid management of post-operative adult respiratory distress syndrome. Surg. Clinics of N. Amer. 65:931–963, 1986.
2. Lenfant C: Respiratory Disease Task Force Report on Problems, Research Approaches and Needs. Department of Health, Education and Welfare, Washington, D.C. U.S. Government Printing Office, Publication Number (NIH) 73-471, 1977.
3. Emerson T. E. Jr., Fournel M. A., Leach W. J., Redens T. B.: Protection against disseminated intravascular coagulation and death by antithrombin-III in the Escherichia coli endotoxemic rat. Circ. Shock 21:1–13, 1987.
4. Abildgaard U., Fargerhol M. K., Egeberg O: Comparison of progressive antithrombin activity and the concentration of three thrombin inhibitors in human plasma. Scand. J. Clin. Lab. Invest. 26:349–354, 1970.
5. Bick R. L., Dukes M. L., Wilson W. L., Fekete L. F.: Anti-thrombin-III (AT-III) as a diagnostic aid in disseminated intravascular coagulation. Thromb. Res. 10:721–729, 1977.
6. Bick R. L., Bick M. D., Fekete L. F.: Antithrombin-III patterns in disseminated intravascular coagulation. Am. J. Clin. Pathol. 73:577–583, 1980.
7. Blauhut B, Necek S, Kramar H. Vinazzer H, Bergmann H: Activity of antithrombin-III and effect of heparin on coagulation in shock. Thromb. Res. 19:775–782, 1980.
8. Lundsgaard-Hansen P., Pappova E.: Humoral defense parameters in massively transfused and septic patients. IN: Collins J. A., Murawski K., Shafer A. W. (eds): "Massive Transfusion in Surgery and Trauma". New York: Alan R. Liss, Inc., 1982, p. 111.
9. Steubjerg S., Pedersen E. B., Laursen H.: Coagulation, fibrinolytic and antithrombin-III profiles monitored in severely infected patients. Thromb. Res. 31:635–640, 1983.
10. Mammen E. F., Miyakawa T., Phillips T. F., Assarian G. S., Brown J. M., Murano G.: Human antithrombin concentrates and experimental disseminated intravascular coagulation. Semin. Thromb. Hemost. 11:373–383, 1985.

11. Emerson T. E. Jr, Redens T. B., Collins M. S.: Antithrombin-III protects against disseminated intraveascular coagulation (DIC in Klebsiella peritonitis. Clin. Res. 35(1)143A, 1987 [Abstract].
12. Emerson T. E. Jr., Redens T. B., Leach W. J., Fournel M. A.: Antithrombin-III treatment limits disseminated intravascular coagulation in endotoxemia. Circ. Shock (Submitted).
13. Esbenshade A. M., Newman J. H., Lams P. M., Jolles H., Brigham KL: Respiratory failure after endotoxin infusion in sheep: lung mechanics and fluid balance. J. Appl. Physiol. 53:967–976, 1982.
14. Brigham K. L., Begley C. J., Bernard G. R., Hutchison A. A., Loyd J. E., Lucht W. D., Meyrick B., Newman J. H., Niedermeyer M. E., Ogletree M. L., Sheller J. R., Snapper J. R.: Septicemia and lung injury. Clin. Lab. Med. 3:719–744, 1983.
15. Bernard G. R., Lucht W. D., Niedermeyer M. E., Snapper J. R., Ogletree M. L., Brigham K. L.: Effect of N-acetylcysteine on the pulmonary response to endotoxin in the awake sheep and upon in vitro granulocyte function. J. Clin. Invest. 73:1772–1784, 1984.
16. Snapper J. R., Hutchison A. A., Ogletree M. L., Brigham K. L.: Effects of cyclooxygenase inhibitors on the alternations in lung mechanics caused by endotoxemia in the unanesthetized sheep. J. Clin. Invest. 72:63–76, 1983.
17. Heflin A. C., Brigham K. L.: Prevention by granulocyte depletion of increased lung vascular permeability of sheep lung following endotoxemia. J. Clin. Invest. 68:1253–1260, 1981.
18. Cochrane C. G., Spragg R., Revak S. D.: Pathogenesis of the adult respiratory distress syndrome. J. Clin. Invest. 71:754–761, 1983.
19. McGuire W. W., Spragg R. G., Cohen A. B., Cochrane C. G.: Studies on the pathogenesis of the adult respiratory distress syndrome. J. Clin. Invest. 69:543–553, 1982.
20. Jochum M., Lander S., Heimburger N., Fritz H.: Effect of human granulocyte elastase on isolated human antithrombin III. Hoppe-Seylers Z Physiol. Chem. 362:103–112, 1981.
21. Carrell R. W., Owen M.C.: Plakalbumin, alpha 1-antitrypsin, antithrombin and the mechanism of inflammatory thrombosis. Nature 317:730–732, 1985.
22. Duswalt K-H., Jochum M., Schramm W., Fritz H.: Released granulocytic elastase: An indicator of pathobiochemical alterations in septicemia after abdominal surgery. Surgery 98:892–899, 1985.
23. Miller-Andersson M., Borg H., Andersson L. O.: Purification of antithrombin-III by affinity chromatography. Thromb. Res. 5:439–452, 1974.
24. Coan M. H., Brockway W. J., Eguizabal H., Kreig T., Fournel M. A.: Preparation and properties of alpha-1-proteinase inhibitor concentrate from human plasma. Vox Sang. 48:333–342, 1985.
25. Staub N. C., Bland R. D., Brigham K. L., Demling R., Erdmann A. J. III, Woolverton W. C.: Preparation of chronic lung lymph fistulas in sheep. J. Surg. Res. 19:315–320, 1975.
26. Roos P. J., Wiener-Kronish J. P., Albertine K. H., Staub N. C.: Removal of abdominal sources of caudal mediastinal node lymph in anesthetized sheep. J. Appl. Physiol. 55:996–1001.
27. Demling R., Smith M., Gunther R., Gee M.: The effects of prostacyclin infusion on endotoxin-induced lung injury. Surgery 89: 257–263, 1981.
28. Huttemier P. C., Watkins W. D., Peteson M. B., Zapol W. M.: Acute pulmonary hypertension and lung thromboxane release after endotoxin infusion in normal and leukipenic sheep. Circ. Res. 50:688–694, 1982.
29. Adams T. Jr, Traber D. L.: The effects of cyclooxygenase inhibition on the cardiopulmonary response of endotoxin. Circ. Shock 9:481–489, 1982.
30. Shasby D. M., Fox R. B., Harada R. N., Repine J. E.: Reduction of the edema of acute hyperoxic lung injury by granulocyte depletion. J. Appl. Physiol. 52: 1237 44, 1982.
31. Flick M. R., Perel A., Staub N. C.: Leukocytes are required for increased lung microvascular permeability after microembolization in sheep. Circ. Res. 48:344–351, 1981.
32. Lowenstein E., Cooper J. D., Erdman A. J., et al: Lung and heart water accumulation associated with hemodilution. Curr. Stud. Hematol. Blood Transf. 41:190–202, 1975.
33. Yoffey J. M., Courtice F. C.: Lymphatics, lymph and the lymphomyeloid complex. London-/Academic, pp. 283 295, 1970.
34. Staub N. C., Pulmonary edema. Physiol. Rev. 54:678 811, 1974.
35. Staub N. C.: The pathogenesis of pulmonary edema. Progress Cardiovascular Dis. 23:53–80, 1980.
36. Erdmann A. J. III, Vaughan T. R. Jr., Brigham K. L., et al: Effect of increased vascular pressure on lung fluid balance in unanesthetized sheep. Circ. Res. 37:271–284, 1975.
37. Blake L. H., Staub N. C.: Pulmonary vascular transport in sheep. A mathematical model. Microvasc. Res. 12:197–220, 1976. 38. McNamee JE, Staub NC: Pore models of sheep lu
38. McNamee J. E., Staub N. C.: Pore models of sheep lung microvascular barrier using new data on protein tracers. Microvasc. Res. 18:229–244, 1979.
39. Carrell R. W.: Reactive-center variants of alpha-1-antitrypsin. A new range of anti-inflammatory agents. Biotechnol. Genet. Eng. Rev. 4:291–309, 1986.
40. Emerson T. E. Jr., Jordan R. E., Redens T. B., Fournel M. A.: Functional activity of antithrombin-III is required for protection in the *E. coli* endotoxemic rat. Circ. Shock (in press).
41. Emerson T. E. Jr., Jordan R. E.: Changes in concentration and activity of antithrombin-III in endotoxemic rats with and without antithrombin-III supplementation. Clin. Res. 34(4):922A, 1986 [Abstract].
42. Blauhut B. Kramar H., Vinazzer H., Bergmann H.: Substitution of antithrombin-III in shock and DIC: A randomized study. Thromb. Res. 39:81–89, 1985.
43. Friedman K. D., Borok Z., Owen J.: Heparin cofactor activity and antithrombin-III antigen levels in pre-eclampsia. Thromb. Res. 43:409–416, 1986.
44. Esmon C. T.: Biochemistry, physiology and clinical implications. Blood 62:1155–1158, 1983.
45. Nawroth P. P., Handley D., Stern D. M.: The multiple levels of endothelial cell-coagulation factor interactions. Clin. Haematol 15:293–321, 1986.
46. Haddy F. J., Emerson T. E. Jr., Scott J. B., Daugherty R. M. Jr.: Kinins and the cardiovascular system. IN: Erdos E. G. (ed.): "Handbook of Experimental Pharmacoloty". Berlin: Springer Verlang, p. 326, 1970.

We claim:
1. A method for decreasing lung damage in a mammal which results following the onset of gram negative septicemia/endotoxemia or from other inflamatory disease state which comprises parenterally administering to said mammal therapeutically effective amounts of antithrombin III and alpha-1-proteinase inhibitor.

2. The method of claim 1 wherein the gram negative septicemia/endotoxemia is a result of an endotoxin selected from the group consisting of *Escherichia coli, Klebsiella pneumoniae* and *Pseudomonas aeruginosa.*

3. The method of claim 1 wherein said antithrombin III and alpha-1-proteinase inhibitor are administered intramuscularly.

4. The method of claim 1 wherein said antithrombin III and alpha-1-proteinase inhibitor are administered intravenously.

5. The method of claim 1 wherein the therapeutically effective dose increases the plasma functional activity of antithrombin III to above 100% of normal.

6. The method of claim 1 wherein the therapeutically effective dose increases the level of alpha-1-proteinase inhibitor to above 100% of normal.

7. A. method for decreasing lung damage in a mammal following the onset of gram negative septicemia/endotoxemia, or other inflammatory disease state, the method comprising
   (a) identifying the condition of gram negative septicemia/endotoxemia, or other inflamatory disease state, and
   (b) administering parenterally, the combined therapy of antithrombin III and alpha-1-proteinase inhibitor.

8. The method of claim 7 wherein said combined therapy is administered in at least two treatment doses to maintain the plasma levels of antithrombin III and alpha-1-proteinase inhibitor at therapeutically effective levels.

9. A method of treating adult respiratory distress syndrome (ARDS) in mammals comprising parentally administering to said mammals therapeutically effective amounts of antithrombin III and alpha-1-proteinase inhibitor.

* * * * *